(12) United States Patent
Springer et al.

(10) Patent No.: US 11,698,375 B2
(45) Date of Patent: Jul. 11, 2023

(54) METHOD FOR PRODUCING AN EXAMINATION REAGENT AND KIT FOR ANALYSING A T-CELL FREQUENCY

(71) Applicant: CONSTRUCTOR UNIVERSITY BREMEN GGMBH, Bremen (DE)

(72) Inventors: Sebastian Hartmut Springer, Bremen (DE); Sunil Kumar Saini, Kerala (IN)

(73) Assignee: CONSTRUCTOR UNIVERSITY BREMEN GGMBH, Bremen (DE)

(*) Notice: Subject to any disclaimer, the term of this patent is extended or adjusted under 35 U.S.C. 154(b) by 952 days.

(21) Appl. No.: 16/458,203

(22) Filed: Jul. 1, 2019

(65) Prior Publication Data

US 2019/0331681 A1 Oct. 31, 2019

Related U.S. Application Data

(63) Continuation of application No. 14/370,217, filed as application No. PCT/DE2013/100001 on Jan. 3, 2013, now Pat. No. 10,386,367.

(30) Foreign Application Priority Data

Jan. 4, 2012 (DE) ..................... 20 2012 100 019.9
Feb. 8, 2012 (DE) ..................... 10 2012 101 028.5

(51) Int. Cl.
*G01N 33/566* (2006.01)
*C07K 14/74* (2006.01)
*G01N 33/569* (2006.01)

(52) U.S. Cl.
CPC ..... *G01N 33/566* (2013.01); *C07K 14/70539* (2013.01); *G01N 33/56977* (2013.01); *G01N 2333/70539* (2013.01)

(58) Field of Classification Search
None
See application file for complete search history.

(56) References Cited

U.S. PATENT DOCUMENTS

2003/0228258 A1 12/2003 Scheinberg et al.
2008/0145378 A1 6/2008 Ovaa et al.

FOREIGN PATENT DOCUMENTS

DE 20 2010 003 498 U1 12/2011
EP 1 683 808 A1 7/2006

OTHER PUBLICATIONS

HLA Nomenclature 2015 (Year: 2015).*
Saini et al (PNAS, Sep. 17, 2013, 110(38): 15383-15388) (Year: 2013).*
Glithero et al (JBC, 2006 281(18): 12699-12704) (Year: 2006).*
Saini et al (PNAS, Sep. 17, 2013, 110(38): 15383-15388) (Year: 2015).*
Saini et al (PNAS, 2015, 112(1): 202-207) (Year: 2015).*
Anjanappa et al (Nature Comm., 2020, 10.1038/s41467-020-14862-4: pp. 1-11) (Year: 2020).*
Ostermeir et al (Mol. Immunol. 2015, 63: 312-319) (Year: 2015).*
Jantz-Naeem and Springer (Curr. Opin. Immunol. 2021, 70: 82-89) (Year: 2021).*
Hafstrand et al (PNAS, 2019, 116: 5055-5060) (Year: 2019).*
B. Rodenko et al.: "Generation of peptide-MHC class I complexes through UV-mediated ligand exchange", Nature Protocols, vol. 1, No. 3, pp. 1120-1131 (2006).
M. Toebes et al.: "Design and use of conditional MHC class I ligands", nature medicine, vol. 12, No. 2, pp. 246-251 (2006).
B. Rodenko et al.: "Class I Major Histocompatibility Complexes Loaded by a Periodate Trigger", J. Am. Chem. Soc., vol. 131, No. 34, pp. 12305-12313 (2009).
P. V. K. Praveen et al.: "Tapasin edits peptides on MHC class I molecules by accelerating peptide exchange", Eur. J. Immunol., vol. 40, pp. 214-224 (2010).
M. Zacharias et al.: "Conformational Flexibility of the MHC Class I $\alpha_1$-$\alpha_2$ Domain in Peptide Bound and Free States: A Molecular Dynamics Simulation Study", Biophysical Journal, vol. 87, pp. 2203-2214 (2004).
A. H. Bakker et al.: "Conditional MHC class I ligands and peptide exchange technology for the human MHC gene products HLA-A1, -A3, -A11, and -B7", PNAS, vol. 105, No. 10, pp. 3825-3830 (2008).
S. R. Hadrup et al.: "High-throughput T-cell epitope discovery through MHC peptide exchange", Methods Mol. Biol., vol. 524, Abstract of pp. 383-405 (2009).
"Human MHC class I histocompatibility antigen HLA-B (HLA-B-4803 allele) mRNA, complete cds", GenBank U09912 1, Nucleotide Alphabet of Life, pp. 1-2 (2000).
H. Cohen et al.: "In Vivo Expression of MHC Class I Genes Depends on the Presence of a Downstream Barrier Element", PLOS ONE, vol. 4, No. 8, e6748, pp. 1-16 (2008).
M.-Y. Sun et al.: "MHC class I multimers", Arthritis Res., vol. 3, pp. 265-269 (2001).
L. Chen et al.: "Endolysosomal Processing of Exogenous Antigen into Major Histocompatibility Complex Class I-Binding Peptides", Scandinavian Journal of Immunology, vol. 59, pp. 545-552 (2004).
Y. Kuniyasu et al.: "Blocking intrahepatic deletion of activated CD8+ T cells by an altered peptide ligand", Cellular Immunology, vol. 238, pp. 31-37 (2005).

* cited by examiner

*Primary Examiner* — Michael Szperka
*Assistant Examiner* — Marianne DiBrino
(74) *Attorney, Agent, or Firm* — Norman B. Thot

(57) ABSTRACT

A method for producing an examination reagent includes adding a helper ligand to a receptor protein which is unfolded in an initial solution so as to provide a pre-solution of the examination reagent with a receptor protein which is folded. The receptor protein which is folded comprises a bonded helper ligand which can be exchanged with an examination peptide.

8 Claims, 1 Drawing Sheet

Specification includes a Sequence Listing.

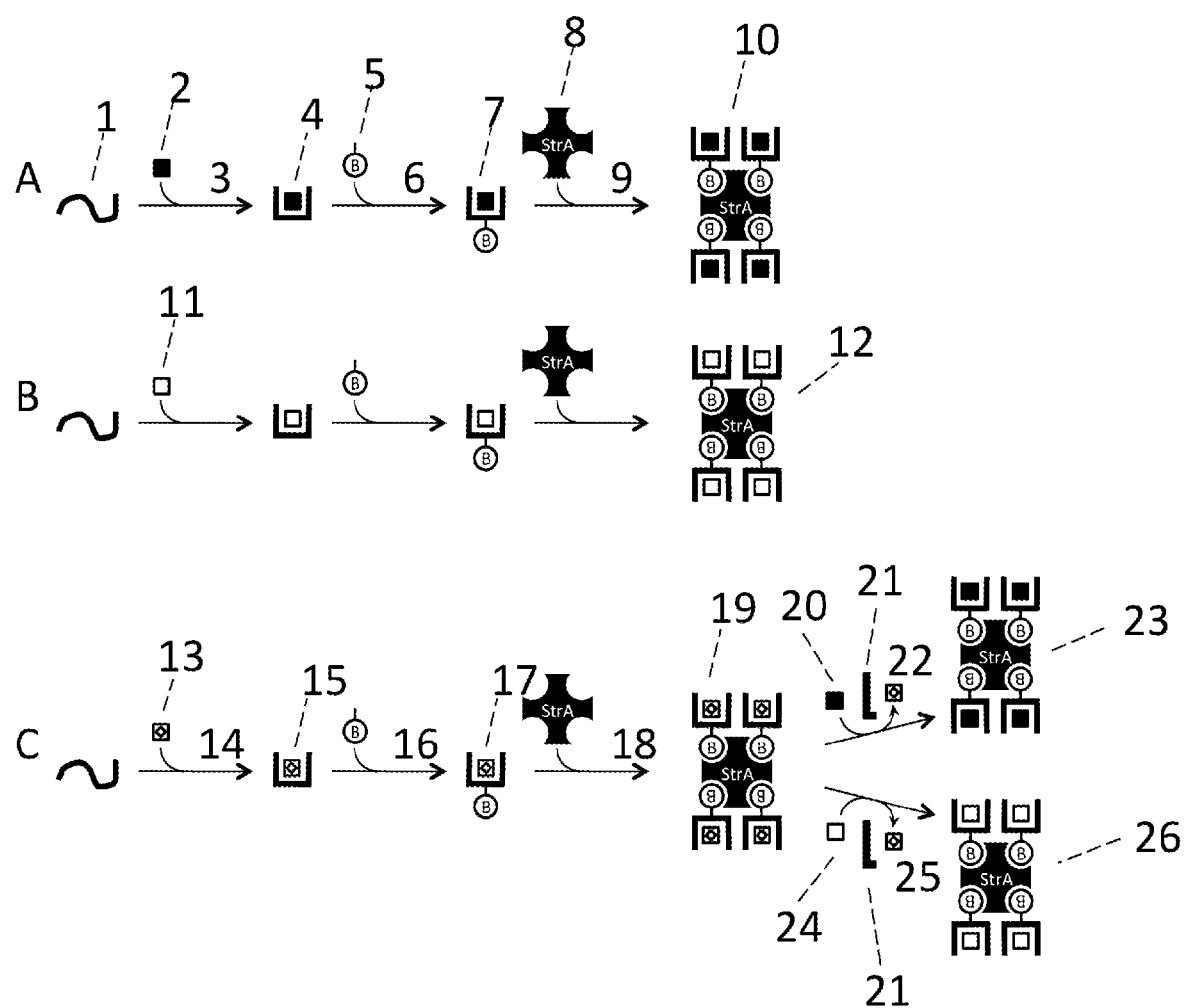

METHOD FOR PRODUCING AN EXAMINATION REAGENT AND KIT FOR ANALYSING A T-CELL FREQUENCY

CROSS REFERENCE TO PRIOR APPLICATIONS

This application is a continuation of application Ser. No. 14/370,217, filed on Jul. 2, 2014, which is a U.S. National Phase application under 35 U.S.C. § 371 of International Application No. PCT/DE2013/100001, filed on Jan. 3, 2013 and which claims benefit to German Patent Application No. 20 2012 100 019.9, filed on Jan. 4, 2012, and to German Patent Application No. 10 2012 101 028.5, filed on Feb. 8, 2012. The International Application was published in German on Jul. 11, 2013 as WO 2013/102458 A1 under PCT Article 21(2).

FIELD

The present invention relates to a method for producing an examination reagent, a multimer, a pre-solution examination reagent, an examination reagent, an analysis solution, a kit, a method for obtaining an analysis result, and an analysis result.

BACKGROUND

MHC class I proteins (MHC class I molecules, Major Histocompatibility Complex Class I molecules, Major Histocompatibility Complex Class I proteins) are transmembrane proteins of the cellular immune response, which bind antigenic peptides from the cell interior of an antigen-presenting cell (APC), such as e.g., from the cytosol or the lumen of endocytic organelles, and present them to the cytotoxic T-cells (CTL, cytotoxic T lymphocytes, killer T cells, CD8 positive lymphocytes) at the cell surface. This is referred to as a so-called class I antigen presentation.

Binding a T-cell receptor (TCR) of a CTL to a class I peptide complex of an APC leads to the activation of the CTL and/or to the induction of cell death (apoptosis) of the APC by the CTL (depending on the location of the reaction in the body, the type of APC (B-cell, dendritic cell, etc.) and the activation state of the CTL).

The specificity (ability to react with a certain class I peptide complex) of a CTL is based on the fact that it carries only one type of TCR (i.e., only TCRs of a single distinct sequence). The immune response is effective because such CTLs, which react with "self"-peptides (peptides produced from the body's own proteins) are eliminated in the thymus.

For this reason, the identification of an antigenic peptide by the TCR of a CTL means that the APC produces foreign proteins, which could stem from viruses or intracellular parasites (bacteria, protozoa). An overproduction of endogenous peptides in malignant degenerated cells, e.g., in tumors, can also lead to such identification reactions.

Almost all proteins present in the cell are broken down into peptides, which subsequently bind with MHC class I proteins in the endoplasmic reticulum (an organelle enclosed by a membrane inside the cell). The complex formed by the peptide and the MHC class I protein (herein referred to as class I peptide complex) is subsequently transported to the surface of the cell where it is available for identification by CTLs.

If novel or mutated proteins are produced due to a tumorigenic malignant degeneration, or if viral or bacterial proteins are produced from the genetic material of a virus or bacteria in case of a viral or bacterial infection, these "novel" proteins are also broken down into peptides, which are then presented in a complex with MHC class I proteins at the cell surface. These "novel" peptides are different from the cell's own peptides and trigger identification by the CTL.

The presentation by MHC class I proteins is also important in allergic reactions, the rejection of transplants, and a number of autoimmune diseases such as multiple sclerosis and spondyloarthropathies (Bechterew's disease or rheumatoid arthritis).

The examination of the immune responses mediated by MHC class I proteins often requires detecting the CTLs that react with a specific class I peptide complex (epitope). Reactions to a single immunodominant epitope often represent 10-20% of the total T-cell population in an organism, so that tracing the T-cell frequency (i.e., the share of CTLs that react with a specific epitope in the total amount of CTLs in the organism) allows following precisely the immune response (e.g., the success or failure of a therapy). Reagents that can identify the epitope specificity of CTLs are therefore indispensable.

Recombinant MHC class I proteins are currently used to detect such epitope-specific CTLs. These proteins are produced in bacteria and are provided as insoluble inclusion bodies that are first denatured in a solution of a chaotropic agent. The chaotropic agent is then removed in the presence of the desired peptide and the class I peptide complex is separated from the unfolded protein by gel filtration chromatography (if necessary). Since the low affinity of a single class I peptide complex with a single TCR does not lead to a tight binding, multimers of class I peptide complexes are used, which, due to the avidity effect, bind tightly enough with the TCR of a CTL to allow for a durable bond.

Such multimers are obtained, for example, by streptavidin-mediated tetramerization of biotinylated class I peptide complexes (class I tetramers), by pentamerization by self-assembling coiled-coil domains (class I pentamers), or by multimerization on dextran (class I dextramers). There are other methods for oligomerization or multimerization of class I peptide complexes.

In general, class I multimers are labelled with fluorescent dyes, which allow them to be detected by microscopic or flow cytometric detection. Epitope-specific CTLs can thus be directly colored for the purpose of detection.

Other uses for recombinant class I peptide complexes are:
  In vitro—Selection and expansion of monospecific T-cells for reinfusion in case of cancer and viral diseases. The selection can be carried out by cytofluorometry (flow cytometry, FACS), by magnet-activated cell sorting (MACS) or, for an increased throughput, in microarrays.
  Ex vivo—Isolation and expansion of CTLs for adoptive therapy after allogeneic stem cell transplant.
  Ex vivo—Removal of alloreactive T-cells after peripheral stem cell transplantation. The removal of autoreactive T-cells, which cause type 1 diabetes, arthritis and other autoimmune diseases, is also interesting, as has already been described with regard to MHC class II reagents. Using isotopically labelled multimers is described in US 2003/0228258 A1.

The production of recombinant class I peptide complexes is complicated, time-consuming and expensive. On the one hand, several thousand MHC class I allotype are known (of which admittedly five alleles of HLA-A cover approximately 50% of the world's population). First and foremost, however, a new multimer must be produced for each antigenic peptide that is to be examined as an epitope so that new multimers, which must be specifically produced as required, are needed for each patient or for each experiment.

It would be simpler to produce the multimers without the antigenic peptides and to subsequently add the respectively required antigenic peptides as necessary. This has not, however, to date been possible because folding MHC class I proteins without an antigenic peptide is not possible for most MHC class I allotypes.

A method involving a special peptide was previously described, where the special peptide is decomposed by a UV treatment or a periodate treatment, and can then be replaced by an added examination peptide (publication: Rodenko et al., Nature Protocols 1 (2006), p. 1120).

This method is expensive, complicated and does not work with all antigenic peptides or class I allotypes.

SUMMARY

An aspect of the present invention is to simplify the production of class I peptide complexes.

In an embodiment, the present invention provides a method for producing an examination reagent which includes adding a helper ligand to a receptor protein which is unfolded in an initial solution so as to provide a pre-solution of the examination reagent with a receptor protein which is folded. The receptor protein which is folded comprises a bonded helper ligand which can be exchanged with an examination peptide.

BRIEF DESCRIPTION OF THE DRAWING

The present invention is described in greater detail below on the basis of embodiments and of the drawing in which:

The FIGURE shows, in A, a schematic representation of the production principle of a multimer (here a tetramer) of MHC class I proteins in a complex with an examination peptide (2) according to the prior art, in B, a schematic representation of the production principle of a multimer (here a tetramer) of MHC class I proteins according to the prior art just as in A, but with another examination peptide (11), and, in C, a schematic representation of the production principle of two multimers (here tetramers) of MHC class I proteins, with different examination peptides (20 and 24), by means of the method according to the present invention.

SEQUENCE LISTING

The Sequence Listing associated with this application is filed in electronic form via EFS-Web and is hereby incorporated by reference into this specification in its entirety. The name of the text file containing the Sequence Listing is Sequence_Listing_1401A. The size of the text file is 881 Bytes, and the text file was created on Jul. 4, 2014.

DETAILED DESCRIPTION

In an embodiment, the present invention provides a method for producing an examination reagent, wherein a helper ligand, which enables the folding of the receptor protein, for example, the MHC class I protein, is added to an initial solution containing a receptor protein or receptor protein complex, more specifically, an unfolded MHC class I protein or a multimeric MHC class I protein complex. The examination peptide and, for example, a ligand exchanger/ligand releaser, is added to the folded MHC class I protein or multimeric MHC class I protein complex in a pre-solution thus produced so that an analysis solution of the examination reagent is obtained which has a folded MHC class I protein with an examination peptide bonded to it. The examination peptide may also be referred to as an "antigenic peptide" in the following.

The advantages of this approach are that an examination reagent can be produced more easily, more quickly, and at lower cost. The idea underlying the present invention is using a helper ligand which can be displaced out of the complex with the receptor protein without requiring a previous splitting of the helper ligand, for example, by means of high-energy radiation or aggressive chemicals. According to the present invention, differences in concentration and/or affinity are used in order to achieve a displacement of the helper ligand.

The "receptor protein" is more specifically an MHC class I protein.

An "MHC class I protein" is a main histocompatibility complex class I protein (also referred to as MHC class I molecule, main histocompatibility class I protein), which is a transmembrane protein of the cellular immune response. These MHC class I proteins bind peptides from the cell interior, such as, for example, from the cytosol or the lumen of endocytic organelles. They also present a peptide antigen to the cytotoxic T-cells at the cell surface (antigen presentation). Human MHC class I proteins are also referred to as HLA proteins (HLA=human leukocyte antigen).

The term "MHC class I protein" here also includes protein, which are structurally and/or functionally similar to the actual MHC class I proteins and which are also encoded in the MHC and which also bind peptides, namely HLA-E, HLA-F and HLA-G. The term also includes fragments of all these proteins, more specifically, the extracellular domain, provided they bind peptides. The term here also includes the heavy chains (large subunits) of the MHC class I proteins, as well as the invariant small subunits (light chain) normally bound to it within the cell, also known as the "beta 2 microgloguline" protein ($\beta$2m), as well as the complex formed by the heavy and light chains. The term also includes a fusion protein that consists of the heavy chain (or a fragment of the heavy chain), a linker (more specifically, the glycine-glycine-glycine-serine-glycine-glycine-glycine-serine-glycine-glycine-glycine-serine-sequence, see SEQ ID NO: 1) and the light chain. "Fragment" here refers more specifically to cohesive partial sequences of at least 10, 15, 20, 25, 30, 35, 40, 45, 50, 60, 65, 70, 80, 90 or at least 100 amino acids, for example, at least 110, 120, 130, 140, 150, 160, 170, 180, 190, or at least 200 amino acids.

The term "MHC class I protein" also includes MHC class I proteins of non-human species of vertebrates. MHC class I proteins of non-human species of vertebrates play a role in the examination and healing of diseases of these species of vertebrates, for example, in veterinary medicine and in animal tests in which human diseases are examined on an animal model, for example, EAE (experimental autoimmune encephalomyelitis) in mice (*Mus musculus*), which is an animal model of the human disease multiple sclerosis. Non-human species of vertebrates are, for example, and more specifically mice (*Mus musculus*), rats (*Rattus norvegicus*), cows (*Bos taurus*), horses (*Equus equus*) and green monkeys (*macaca* mulatta). MHC class I proteins of mice are, for example, referred to as H-2-proteins, which are encoded by the gene loci H2K, H2L and H2D. A specific allotype of a mouse MHC class I protein is, for example, H2K$^b$ or H2L$^d$.

A "folded protein" must be understood as a protein with a conformation (three-dimensional structure) which is stable (i.e., not substantially changeable over the course of a few hours) and an intact biological activity (for example, binding of the peptide). In contrast, an "unfolded protein" must be understood as a protein with a conformation that does not fulfil these two criteria. A "folded protein" must be more specifically understood as a receptor protein with a conformation in which the receptor protein binds peptides in vivo.

The term "peptide" as used herein refers to peptides and peptide-like chemical compounds, more specifically, such compounds that bind with MHC class I proteins, even more specifically, such compounds that are recognized by CTL in a complex with MHC class I proteins.

The term "examination peptide" must be understood more specifically as peptides having a high affinity (i.e., a dissociation constant $K_D \leq 1$ μM, for example, ≤500 nM, for example, ≤300 nM, ≤200 nM or ≤100 nM) with the receptor protein. Examination peptides are peptides having an amino acid sequence, which is typically determined by the examination to be undertaken or by the application, for example, a disease to be examined or other diagnostic purposes, and can differ from one examination to the next. Examination peptides typically have a length of 8, 9, 10 or 11, for example, 9 or 10 amino acids.

Helper ligands, here also synonymously referred to as "helper peptides", are peptides or peptide-like chemical compounds that bind with a high affinity (i.e., with a dissociation constant $K_D \leq 1$ μM) with the receptor protein, for example, an MHC class I protein and which cause or promote folding of the MHC class I protein from the unfolded state or stabilization of the folded MHC class I protein. Helper ligands have a length of, for example, 2, 3, 4, 5, 6, 7, 8, 9, 10 or 11, for example, 8, 9, 10 or 11, for example, 8 or 9 amino acids. Helper ligands can, for example, have a lower affinity with receptor proteins than the examination peptides to be used. The difference can, for example, always have a range so that the dissociation constant of the helper ligand amounts, for example, to $K_D$=500 nM when the dissociation constant of the examination peptide amounts to $K_D$=50 nM.

The exchange can, for example, occur by adding a ligand exchanger/ligand releaser and the antigenic examination peptide to the solution of a receptor protein or receptor protein complex, for example, an MHC class I protein or multimer. The ligand exchanger/ligand releaser facilitates the exchange of a helper ligand by an examination peptide in the analysis solution or, as the case may be, makes it possible, so that the MHC class I protein in the analysis solution contains, i.e., binds, the examination peptide.

The exchange, and a subsequent separation of the MHC class I protein or multimer from the helper ligand and, if necessary, the ligand exchanger/ligand releaser can, for example, takes place in incubation at a temperature between 4° C. and 40° C. for a time period between 1 minute and 60 minutes. This separation can be more particularly carried out by flow chromatography, more specifically, gel filtration chromatography, or affinity chromatography.

Without intending to be bound by a particular theory, it is assumed that the displacement reaction in the presence the ligand exchanger/ligand releaser takes place so that in the course of the equilibrium reaction between binding and unbinding the helper ligand clears a part of the peptide binding site of the MHC class I protein or dissociates itself from it, and that in the next step the ligand exchanger/ligand releaser occupies and/or binds to this part of the peptide binding site of the MHC class I protein, and that in the next step the helper ligand cannot bind again with the corresponding part of the peptide binding site of the MHC class I protein and therefore remains bound only partially or with a part of its structure to the MHC class I protein, that the helper ligand subsequently completely detaches from the peptide binding site of the MHC class I protein, whereby a free peptide binding site of the MHC class I protein is created, to which the examination peptide binds in the following step, whereby a complex of an MHC class I protein and the examination peptide is formed.

The ligand exchanger/ligand releaser is or includes more specifically an amino acid and specifically a modified amino acid. An amino acid is a chemical compound, which contains an amino or ammonium group ($-NH_2$ or $-NH_3^+$) attached to a carbon (C) atom and simultaneously contains a carboxyl or carboxylate group ($-COOH$ or $-COO^-$) attached to the same or another carbon atom. Examples of an amino acid include glycine, alanine, homoleucine, beta-alanine and ε-acetyl-lysine. In the present, it is assumed that an amino acid is modified when the amino group has reacted with another chemical compound (for example, a carboxylic acid or one of its derivatives) so that this other chemical compound is covalently bonded with the amino group, for example, via an amide bond (peptide bond, lactam bond) or a bond similar to an amide bond (for example, a thioamide bond). In the present, it is also assumed that an amino acid is modified when the carboxyl group has reacted with another chemical compound (for example, an alcohol, an amine, or one of their derivatives) so that this other chemical compound is covalently bonded with the carboxyl group, for example, via an ester bond or via an amide bond or via a bond similar to an ester or amide bond. In the present, it is also assumed that an amino acid is modified when the amino group as well as the carboxyl group have reacted within the meaning of the present section. Examples of modified amino acids are acetyl methionine, alanine amide and N-acetyl-tryptophan-amide.

The ligand exchanger/ligand releaser can also be or include a peptide, which is characterized in that it consists of several amino acids, which are connected to each other by amide bonds (peptide bonds) like in a protein, or which are connected to each other by bonds similar to amide bonds, for example, thioamide bonds. In the present, it is also assumed that the ligand exchanger/ligand releaser is a peptide when the amino terminal amino group or the carboxyl terminal carboxyl group or the nitrogen atom of a previously described internal amide bond has reacted with other compounds.

The ligand exchanger/ligand releaser can moreover be or include a peptide-like chemical compound. "Peptide-like chemical compounds" are, for example, chemical compounds, in which the internal peptide bonds (amide bonds) are replaced by lactams or piperazinones, and also by 7,6-bicyclic pyridizine, 9-amino-octahydro-6,10-dioxo-6H-pyridazino[1,2-a][1,2]diazepine-1-carboxylic-acid, 5-amino-1,2,4,5,6,7-hexahydroazepino[3,2,1-hi]indol-4-one-2-carboxylic-acid and methylbutyl-substituted lactams, more specifically 1-(tert-butyloxycarbonyl)-7-[1-(tert-butyloxycarbonyl)-3-methylbutyl]-6-oxo-1,7-diazaspiro[4.5]decane.

Ligand exchangers/releasers can, for example, be peptides consisting of 1, 2, 3, 4, 5, 6 or 7 amino acids, for example, 2 or 3 amino acids, among which, for example, one amino acid, more specifically, the one at the carboxyl terminus of the peptide, is a modified amino acid.

The ligand exchanger/ligand releaser binds with the receptor protein, for example, the MHC class I protein, for example, with a lower affinity than the examination peptide and, for example, with a lower affinity than the helper ligand. The dissociation constant $K_D$ of an examination peptide can, for example, amount to 100 nM, whereas the dissociation constant $K_D$ of the ligand exchanger/ligand releaser amounts to 10 μM to 10 mM, for example, 1 mM. The difference of binding affinity between the examination peptide and the ligand exchanger/ligand releaser can, for example, amount to approximately two ranges (factor of 100). The helper ligand can have an intermediate binding affinity, for example, a dissociation constant of 1 μM. A lower binding affinity of the ligand exchanger/ligand releaser can be achieved, for example, by using a peptide that is shorter than the examination peptide. The ligand exchanger/ligand releaser can, for example, be a single amino acid or a peptide that consists of 2, 3, 4, 5, 6 or 7 amino acids, for example, 2 or 3 amino acids. When a helper ligand and a ligand exchanger/ligand releaser are used together, a combination in which the helper ligand is a peptide of 8, 9, 10 or 11 amino acids, for example, 9 or 10 amino acids and the ligand exchanger/ligand releaser is a single amino acid or peptide of 2, 3, 4, 5, 6, or 7, for example, 2 or 3 amino acids. In this context, the term "peptide" also comprises peptide-like compounds.

The receptor protein having a helper ligand has the following more specific structure: a MHC class I protein in the folded state, the helper ligand being bonded with the peptide binding side of the MHC class I protein.

In order to provide an effective and large yield of unfolded MHC class I proteins, the unfolded MHC class I protein can be produced in an expression system.

"Expression" is the production of a protein, more specifically, an MHC class I protein (as described before, i.e., the large as well as the small subunits, together, separated, or connected) in an expression system.

In a related embodiment, the expression system can have a bacterial cell, more specifically, an *Escherichia-coli* cell or a yeast cell, more specifically, a *saccharomyces-cerevisiae* cell, or an insect cell, more specifically, a *spodoptera-frugiperda* cell, or a mammalian cell, more specifically, a CHO cell, CHO referring to "Chinese (*Cricetulus griseus*) hamster ovary", or a cell-free expression system, more specifically, as a reticulocyte lysate.

In order to achieve the highest possible yield, the expression system has a plurality of cells, more specifically, a number of cells in the range of at least 1,000,000 cells.

The "examination reagent" must more specifically be understood as a compound, substance, complex or particle, which specifically binds with a TCR of a CTL and which is used for one of the purposes described in the introduction, more specifically, for analyzing a T cell frequency, for positive selection (isolation) of CTL, and for negative selection (removal) of CTL. Examination reagents are, more specifically, multimers such as described in the following, particles (according to the following explanation regarding the multimerization element) and membrane preparations as subsequently described. The term "examination reagent" more specifically refers to a folded receptor protein that has a bonded examination peptide, a multimer comprising at least two such folded receptor proteins with bonded examination peptides, and a substrate, for example, a particle, in, at or on which at least one such receptor protein or multimer is immobilized.

A "specific binding" is a binding that is significantly stronger than the average observable ("non-specific") binding between a randomly chosen TCR and a randomly chosen MHC class I protein, wherein "significantly" means that the dissociation constant $K_D$ of the specific binding is at least ten times lower than that of a non-specific binding.

In another embodiment, a signaling element is attached to the MHC class I protein, wherein the signaling element is more specifically a fluorescent dye. A simple method for identifying the MHC class I protein is thus provided. "Attached" here means covalently or non-covalently bonded.

A fusion element can additionally be attached to the MHC class I protein. A fusion element must be understood as a polypeptide sequence which comprises a protein domain or a part of it. Examples of fusion elements are, more specifically, the $F_c$ domains of antibodies, *Staphylococcus aureus* protein A, or an oligohistidine or oligoarginine sequence, wherein an oligohistidine sequence consists of three to twelve, for example, six, histidines, or such protein domains that have stable coiled-coil interactions with each other, more specifically, the coiled domains of the transcription factors jun and fos. "Attached" here means covalently or non covalently bonded.

The advantage of the fusion element is that it allows for the specific binding of the MHC class I protein with a multimerization element or with a particle. The advantage of the fusion element is also that it allows for the cleaning and the detection of MHC class I proteins by means of techniques in which the fusion element is specifically identified via reagents that specifically bind with it. Another advantage of the fusion element is that it allows for a direct binding of MHC class I proteins with each other.

An anchor element can additionally be attached to the receptor protein. This anchor element is more specifically a biotin molecule which is attached to the protein either by a natural biotinylation sequence genetically encoded in the gene for the MHC class I protein and a biotinylated enzyme, more specifically, BirA, or by means of chemical methods, more specifically, using a N-hydroxysuccinimide derivative., "Attached", for example, here means bonded, for example, covalently or non-covalently.

The advantage of the anchor element is more specifically that it allows for the assembly of MHC class I proteins into multimers and the binding with a particle. The advantage of the anchor element is also that it allows for cleaning and detection of MHC class I proteins by means of techniques in which the anchor element are specifically identified by specific reagents binding with it.

In order to exploit the avidity effect, several folded MHC class I proteins can be assembled into one multimer.

The assembly of the MHC class I protein into a multimer can be carried out, for example, by bringing together an MHC class I protein and a multimerization element.

The "multimerization element" is characterized in that the anchor elements provided on the MHC class I proteins form a non-covalent or covalent binding with the multimerization element.

Avidin or streptavidin are in particular such a "multimerization element".

In other cases, such a multimerization element can be a particle, for example, with a diameter of 1 micrometre to 1 millimetre, consisting, for example, of agarose, which is chemically modified so that the surface of the particle can specifically bind with the anchor elements. Such a chemical modification of the surface can take place by way of a covalent or non-covalent binding of the surface with, for example, avidin or streptavidin or with an antibody that reacts with a part of the MHC class I protein.

The assembly of several MHC class I proteins into a multimer can also take place by way of a binding of the MHC class I proteins with each other without the need for a binding protein.

The "multimer" includes more specifically a tetramer and/or a pentamer and has more specifically two or several MHC class I proteins.

The advantage of the multimer is amongst others that the multimer can be obtainable by filtration or chromatography and that at least two MHC class I proteins are linked to the multimer. Another advantage of the multimer is the so-called avidity effect, which refers to the fact that several MHC class I proteins bind more strongly, i.e., with a lesser dissociation constant $K_D$, with the TCR at the surface of a CTL. This stronger binding facilitates the detection and isolation of CTLs. This stronger binding can additionally induce an activation of the CTL.

An "activation" of the CTL here refers to a modification of the metabolic processes within the CTL caused by the binding of proteins with the TCR of the CTL, more specifically, by the binding of examination reagents, more specifically, MHC class I proteins, multimers, particles or membrane preparations.

In order to provide a simple method of identification, a multimer signaling element can be attached to the multimer, the multimer signaling element being more specifically a fluorescent dye. "Attached" here more specifically refers to the binding, for example, the covalent or non-covalent binding, of the multimer signaling element with the multimer.

The MHC class I proteins can additionally be multimerized in membrane preparations. "Membrane preparation" here refers to lipid membranes, which are characterized in that they contain MHC class I proteins. The MHC class I proteins can be contained in the lipid membranes so that they are partially immersed in the lipid membrane and are held in or on the lipid membrane by hydrophobic interactions; or they can be contained so that they are covalently or non covalently bonded to the surface of the lipid membrane.

"Lipid membranes" refers to such membranes that consist of the cell surface (plasma membrane) of eukaryotic cells or whose structure and composition corresponds substantially to that of the plasma membrane; in this regard, it is irrelevant that the cells are alive or fixed (dead), intact (permeable to water-soluble substances) or not intact. The term also refers to membranes that have been assembled out of isolated components, more specifically, lipids, in a laboratory.

The insertion of the MHC class I proteins into the lipid membrane can be carried out by producing the MHC class I protein in a cell (e.g., in an expression system) and by producing the membrane preparation from this cell. The insertion of the MHC class I protein into the lipid membrane can also be carried out by adding the MHC class I protein to a pre-existing lipid membrane.

The advantage of the membrane preparation is amongst others that the membrane preparation can be obtainable from expression systems and that at least two MHC class I proteins are contained in the membrane preparation. Another advantage of the membrane preparation is the so-called avidity effect, which refers to the fact that several MHC class I proteins bind more strongly, i.e., with a lesser dissociation constant $K_D$, with the TCR at the surface of a CTL. This stronger binding facilitates, more specifically, the detection and isolation of CTLs. This stronger binding can additionally induce an activation of the CTL.

In an embodiment, the present invention provides a folded receptor protein, more specifically, a folded MHC class I protein, which has a helper ligand. By adding the examination peptide and, for example, additionally the ligand exchanger/ligand releaser, a receptor protein, for example, an MHC class I protein, can be provided in an advantageous manner, which binds the examination peptide in exchange for the helper ligand and subsequently comprises the examination peptide.

The helper ligand can, for example, be a peptide consisting of 2, 3, 4, 5, 6, 7, 8, 9, 10 or 11, for example, 8, 9, 10 or 11, for example, 9 or 10 amino acids.

In addition to the helper ligand or instead of the helper ligand, the folded protein can, for example, have a ligand exchanger/ligand releaser that has a lesser affinity with the receptor protein than the helper ligand and/or is an amino acid or a peptide of 2, 3, 4, 5, 6 or 7, for example, 2 or 3 amino acids. A combination in which the helper ligand is a peptide of 8, 9, 10 or 11, for example, 9 or 10 amino acids, and the ligand exchanger/ligand releaser is a single amino acid or a peptide of 2, 3, 4, 5, 6 or 7, for example, 2 or 3 amino acids, can be used.

In an embodiment, the present invention provides a multimer which has folded MHC class I proteins, which have a helper ligand and, for example, also or alternately, a ligand exchanger/ligand releaser according to the present invention. By adding the examination peptide and, for example, the ligand exchanger/ligand releaser, a multimer can be provided in an advantageous manner which binds the added examination peptide in exchange for the helper ligand and subsequently at least partially comprises the examination peptide. Using a multimer allows the advantageous exploitation of the avidity effect, which allows the multimer to bind with the surface of the CTL.

In an embodiment, the present invention provides a particle which has folded MHC class I proteins having helper ligands. By adding the ligand exchanger/ligand releaser and the examination peptide, a particle can be provided which binds the added examination peptide in exchange for the helper ligand and subsequently at least partially comprises the examination peptide. Using a particle allows for the exploitation of the avidity effect, which allows the multimer to bind with the surface of the CTL.

In an embodiment, the present invention provides a membrane preparation which has folded MHC class I proteins having helper ligands. By adding the ligand exchanger/ligand releaser and the examination peptide, a membrane preparation can be provided which binds the added examination peptide in exchange for the helper peptide and subsequently at least partially comprises the examination peptide. Using a membrane preparation allows for the exploitation of the avidity effect, which allows the multimer to bind with the surface of the CTL.

The terms used herein correspond to the above definitions.

In order to achieve an efficient folding of the MHC class I protein on the one hand and an efficient exchange of the helper ligand with the examination peptide on the other hand, the helper ligand can be a modified amino acid or a peptide, which forms a part of an exchangeable and folded MHC class I protein complex. More specifically, a folded MHC class I protein comprising the helper ligand is thus formed.

The "exchangeable MHC class I protein complex" includes a folded MHC class I protein featuring the helper peptide. "Exchangeable" refers to the property of a receptor protein or receptor protein complex allowing for the exchange of a helper ligand bonded with a binding site of the receptor protein or receptor protein complex with an examination peptide.

A "pre-solution examination reagent" includes an exchangeable receptor protein complex, for example, a MHC class I protein complex, i.e., a folded receptor protein having a bonded helper ligand, or in another embodiment, a multimer having folded receptor proteins, for example, MHC class I proteins featuring the helper ligand, or in another embodiment, a particle having folded receptor protein, for example, MHC class I proteins featuring the helper ligand, or in another embodiment, a membrane preparation having folded receptor proteins, for example, MHC class I proteins featuring the helper ligand. A pre-solution examination reagent furthermore includes a ligand exchanger/ligand releaser.

The "folded MHC class I proteins" are defined by the above definition.

The problem can also be solved by a "pre-solution" having a pre-solution examination reagent. An efficient examination method can thereby be provided. A kit with a pre-solution reagent with a pre-solution examination reagent can additionally be produced in accordance with specifications known from the prior art.

In an embodiment, the present invention provides an examination reagent which is produced as described above. An efficient method for isolating T-cells can thus also be provided. An effective method for removing T-cells from a population can also be provided in this manner. The production of an examination reagent from the pre-solution examination reagent thus only requires a simple, quick, and low-cost work step, which can be implemented by a less qualified person, for example, a laboratory assistant or a technical employee.

In an embodiment, the present invention provides for an analysis solution having an examination reagent. An effective examination method can thus be provided as well as a kit containing the analysis solution.

In an embodiment, the present invention provides a kit, more specifically, a kit for analysing a T-cell frequency, containing an examination peptide and a separate pre-solution examination reagent, which has an exchangeable MHC class I protein complex with a bonded helper ligand and, for example, a ligand exchanger/ligand releaser. By exchanging the helper ligand with an examination peptide, for example, by means of the ligand exchanger/ligand releaser, an examination reagent can thus be produced quickly, simply, and at low cost. A laboratory assistant can thereby be provided with a tool for everyday use, by means of which a simple, quick and low cost production of an examination reagent, i.e., a MHC class I protein, multimer, particle or membrane preparation with a bonded examination peptide, is implementable.

The "kit" is more specifically a system which has a set of components allowing for the implementation of a complete analysis, such as, for example, the analysis of a T-cell frequency, for example, without acquiring any additional material.

The "T-cell frequency" refers to the percentage of CTL that identifies a specific peptide in a complex with a specific MHC class I protein. The term "CTL" here refers to the cells defined in the introduction. The T-cell frequency for a peptide faced with an immune response typically lies between 0.01% and 20%.

In an embodiment, the present invention provides a method for obtaining the result of an analysis, wherein an examination peptide, an exchangeable receptor protein, or an exchangeable receptor protein complex, for example, an exchangeable class I protein complex, which contains a helper ligand, and, for example, additionally the ligand exchanger/ligand releaser, are mixed under conditions in which the helper ligand is replaced by the examination peptide.

In the method, the examination peptide and the exchangeable receptor protein can, for example, be mixed together with a ligand exchanger/ligand releaser, wherein the helper ligand, for example, has a lesser affinity with the receptor protein than the examination peptide and the ligand exchanger/ligand releaser has a lesser affinity with the receptor protein than the helper ligand, and/or wherein the helper ligand is a peptide of 2, 3, 4, 5, 6, 7, 8, 9, 10 or 11, for example, 8, 9, 10 or 11, for example, 9 or 10 amino acids, and/or the ligand exchanger/ligand releaser is an amino acid or a peptide of 2, 3, 4, 5, 6 or 7, for example, 2 or 3 amino acids. A combination, in which the helper ligand is a peptide of 8, 9, 10 or 11 amino acids, for example, 9 or 10 amino acids and the ligand exchanger/ligand releaser is a single amino acid or a peptide of 2, 3, 4, 5, 6 or 7, for example, 2 or 3 amino acids, can be used.

Based on the result of the analysis, a doctor can, for example, confirm or exclude a diagnosis.

In an embodiment of the method of the present invention, the analysis solution can be mixed with a cell sample so that the analysis solution complexes with a specific element of the cell sample, thus forming a complex. A "specific element of the cell sample" must be understood as an element that complexes with the receptor protein or receptor protein complex. It can, for example, refer to certain T-cells.

Specific cells can thus be examined.

The term "cell sample" here comprises more specifically blood samples of humans, animals, more specifically, mammalians, up to cartilaginous fish, and more specifically, samples of lymphocytes that have been isolated from blood samples.

"Complexation" is here more specifically the specific binding of the reagent through interactions between atomic elements of the reagent and the cell sample, more specifically, ionic bindings, hydrophobic interactions and hydrogen bonds. In the simplest case, this refers to the specific binding of an MHC class I protein with a peptide on a TCR of a CTL. In another case, this refers to a simultaneous binding of several MHC class I proteins (which can also be contained in a multimer) with several TCRs of a CTL, whereby the so-called "avidity effect", which refers to the fact that the binding of several class I proteins with several TCRs leads to a stronger binding of the multimer with the CTL than the binding of a single MHC class I protein with a single TCR, can be advantageously exploited.

"Mixing" means that the analysis solution and the cell sample are mixed so that a complexation reaction can take place. In the simplest case, the cell sample is put into the analysis solution.

In a related embodiment, a detection of the signaling element occurs after mixing, more specifically, by means of flow cytometry. In doing so, only those signaling elements are detected that have formed a complex with the cells. The cells that have formed a complex with the signaling element are thereby detected.

"Detecting" herein includes all measurable physical parameters. It more specifically includes optical and spectroscopic methods.

This results in the following advantages: all the cells that have formed a complex with the signaling element are detected. The percentage of the cells that have formed a complex with the signaling element can thereby be specified. The percentage of CTLs reacting with a specific MHC class I protein containing a specific examination peptide can thus be determined. The T-cell frequency can thus be specified.

The present invention is hereafter explained based on exemplary embodiments and the enclosed drawing.

The FIGURE schematically shows in A and B the production of a complex of an MHC class I protein tetramer and an examination peptide according to the prior art. The unfolded MHC class I protein 1 is provided with the examination peptide 2, 11 and the folded MHC class I protein 4 with a bonded peptide is formed in a folding process 3. After this, a cleaning step is preferably carried out, more specifically a gel filtration chromatography. An anchor element 5 or a precursor of the anchor element 5, for example, biotin (B) is added, and bonded with the class I protein (6), so that a class I protein 7 with a bonded peptide and a bonded anchor element is obtained. After this, another cleaning step can, for example, be carried out, more specifically, a gel filtration chromatography. In the following step, a multimerization element 8, for example, streptavidin (StrA) is added, so that a multimer 10, 12 is obtained, which features the respective bonded examination peptide 2, 11. After this, another cleaning step can, for example, take place, more specifically, a gel filtration chromatography.

The prior art is characterized in that in order to obtain multimers with different peptides (e.g., 10, 12), the procedure described above must be carried out separately from beginning to end for each multimer.

FIG. 1 C schematically describes a method according to the present invention.

A helper ligand 13 is introduced into the folding reaction 14 and allows for the folding of an MHC class I protein in the denatured state without the presence of an examination peptide, resulting in a folded MHC class I protein 15 with a bonded helper ligand. The steps 16, 18 of attaching the anchor element (16) and producing the multimer (18), including the required cleanings (if applicable), then subsequently take place in the same way as described above with regard to the prior art. A folded MHC class I protein 17 is thus provided with an anchor element (e.g., biotin) and with the helper ligand 13 is first obtained and, after the multimerization step 18 implemented by means of the multimerization element, a multimer 19 is obtained, which comprises MHC class I proteins having the helper ligand 13. This multimer 19 can then be further processed or distributed, for example, as part of a kit.

In order to obtain a multimer with a desired examination peptide, the examination peptide 20, 24 and, for example, a ligand exchanger/ligand releaser 21, is added to the multimer 19 containing the helper ligand 13. An exchange reaction 22, 25 is thereby initiated at the end of which multimers 23, 26 are obtained, which are provided with the respective examination peptide 20, 24.

With this method, class I multimers can be produced and distributed first without an examination peptide. Then, when the multimers are to be used, the examination peptide can be added directly, for example, together with the ligand exchanger/ligand releaser, whereby a ready-to-use class I multimer reagent with a corresponding examination peptide is obtained.

The present invention covers, for example, MHC class I allotypes encoded in the human gene loci for HLA-A, HLA-B and HLA-C. It also covers MHC-class-I-like proteins that are encoded in the human MHC and also bind peptides, i.e., HLA-E and HLA-G. The present invention also covers MHC class I allotypes that are encoded in murine gene loci for H-2K, H-2D and H-2L, as well as class-I-like proteins that are encoded in the murine MHC and also bind peptides, i.e., Qa-1 and Qa-2.

The following applications are, for example, implementable by the present invention: detection of specific T-cells and their frequencies by means of examination reagents; isolation of CTLs with certain specificities by means of examination reagents; activation of CTLs with certain specificities by means of examination reagents. Examination reagents are here more specifically MHC class I proteins, multimers, particles and membrane preparations containing MHC class I proteins, which contain examination peptides that have been exchanged with helper ligands by means of the method according to the present invention, for example, using the ligand exchanger/ligand releaser.

Example 1

The following gives general instructions for producing an MHC class I tetramer by means of the method according to the present invention.

Cloning

In order to introduce the gene sequence of a class I protein into an expression vector, a polymerase chain reaction (PCR) is implemented. The sequence of the forward primer is 5' x-y 3', wherein x is the cut sequence of a restriction enzyme and y is the beginning of the gene of the class I protein (20 base pairs). The sequence of the reverse primer is 5' e-f 3', wherein e is the cut sequence of a restriction enzyme and f is a sequence that is complementary to the end of the gene of the class I protein and also contains the stop codon.

The PCR product is cloned in an expression vector containing a T7 promoter, more specifically, by cutting the ends of the PCR product with restriction enzymes and by cutting the ends of the expression vector with restriction enzymes, which produce overhang sequences fitting the ends of the PCR product, and by subsequent ligation of the PCR product in the expression vectors by means of the enzyme ligase; or by cloning of the PCR product in an expression vector by means of a commercially available PCR cloning kit, more specifically a TOPO TA kit of the company Invitrogen, or a CloneJet™ kit of the company Fermentas. The sequence of the product is then verified by sequencing.

Production of the Expression Strain

The expression plasmid is transformed in an *E. coli* expression strain (e.g., BL21DE3(pLysS)), more specifically, by producing competent cells by treatment of *e. coli* cells with dimethyl sulfoxide or with calcium chloride, incubation of the treated cells with the expression plasmid and selection, on agar plates, of the cells thus transformed, to which the antibiotic has been added, which is catabolized by the enzyme encoded by the resistance gene present on the expression plasmid.

The expression strain is frozen as a liquid culture with 20% glycerol and is storable at −80° C. for several years.

Production of the MHC Class I Protein 20 ml of LB medium with a suitable antibiotic (e.g., 100 μg/ml ampicillin) are inoculated with 100 μl of a preparatory culture of an expression strain of *Escherichia coli* carrying a plasmid with an MHC class I gene and grown over night at 37° C. in a shaking incubator until they reach the stationary phase.

The culture is centrifuged (3000×g, 10 minutes, 25° C.), the supernatant is disposed of and the sediment (cells) are used for inoculation of a 1 liter culture of the same medium. The culture is grown in a shaking incubator at 37° C. up to an extinction of 0.4-0.5 at a wavelength of 600 nm and with a cuvette diameter of 1 cm, the extinction being measured by means of a spectrophotometer (ThermoSpectronic Genesys 10UV).

The culture is mixed with isopropyl-β-D-1-thiogalactopyranoside (IPTG) at a final concentration of 0.5 mM and then grown in the same conditions up to an extinction of 1.0 at a wavelength of 600 nm and with a cuvette diameter of 1 cm, the extinction being measured by means of a spectrophotometer (ThermoSpectronic Genesys 10UV).

The culture is centrifuged (13000×g, 10 minutes, 25° C.), the supernatant is disposed of and the sediment is resuspended in 20 ml of a sucrose solution (25 wt.-% sucrose, 1 mM ethylenediaminetetraacetic acid (EDTA), 1 mM phenylmethylsulfonyl fluoride (PMSF), 10 mM dithiohtreitol (DTT), 10 mM tris(hydroxymethyl)aminomethane (Tris), pH 8.0). The suspension is transferred into a 50 ml centrifuge tube and frozen in a freezer.

Cell Lysis

The centrifuge tube with the cell suspension is thawed in a 30° C. water bath with shaking. After thawing, the work is continued on ice or in a cold room.

Fragmentation of the DNA

The suspension is treated with the probe of an ultrasound device until it no longer looks viscous.

The suspension is centrifuged (40000×g, 15 min, 4° C.), the supernatant is disposed of and the sediment is resuspended with an ultrasound treatment in 20 ml of a detergent buffer (25 wt.-% sucrose, 1 vol.-% triton X-100, 5 mM EDTA, 2 mM DTT, 50 mM Tris, pH 8.0).

The suspension is centrifuged (40000×g, 15 min, 4° C.), the supernatant is disposed of and the sediment is resuspended with an ultrasound treatment in 20 ml of a urea buffer (2 M NaCl, 2 M urea, 2 mM DTT, 25 mM Tris, pH 8.4).

The suspension is centrifuged (40000×g, 15 min, 4° C.), the supernatant is disposed of and the sediment is resuspended with an ultrasound treatment in 20 ml of TBS (150 mM NaCl, 0.5 mM PMSF, 20 mM Tris, pH 7.5).

The suspension is centrifuged (40000×g, 15 minutes, 4° C.), the supernatant is disposed of and the sediment is resuspended with an ultrasound treatment in 10 ml of a denaturing solution (8 M urea, 50 mM 4-(2-hydroxyethyl)-1-piperazineethanesulfonic acid (HEPES), 100 μM β-mercaptoethanol, pH 6.5) and the suspension is incubated with a light shaking for 48 hours at 4° C.

The suspension is centrifuged (40000×g, 15 minutes, 4° C.). The sediment is disposed of and the centrifugation is repeated. The sediment is again disposed of and the clear solution is filtered through a 0.22 μm filter, aliquoted and stored until further use at −20° C. The protein concentration is determined by measuring the extinction at 280 nm as compared to that of water. The extinction coefficient ε of a class I protein in these conditions is approximately 85000 M-1cm-1.

In this manner, the heavy subunit of MHC class I and the light subunit (beta-2-microglobulin, β₂m) are separately produced in two different preparations (and subsequently mixed during folding) or a fusion protein consisting of the heavy and light chain is produced as a single protein.

Folding of the Class I Protein

One liter of a folding buffer (100 mM Tris-Cl pH 8.0, 0.5 M arginine, 2 mM EDTA, 0.5 mM oxidized glutathione, 5 mM reduced glutathione) is mixed dropwise with stirring at 4° C., either with 10 mg of denatured β₂m and 30 mg of the denatured heavy subunit or with 20 mg of a fusion protein consisting of the heavy and light chain in a denatured solution. A helper ligand is also added, typically with a concentration between 100 nM and 1 mM. The solution is continuously stirred for 12 hours.

The solution is concentrated in a pressure filtration device to approximately 100 ml and then in a centrifugal concentration device (cut-off: 30000 Da) to approximately 1 ml and then centrifuged (16000×g, 4° C., 15 min); the sediment is disposed of.

The supernatant is filtered (0.22 μm) and deposited on a gel filtration column (e.g., GE Healthcare HiLoad 16/60 SUPERDEX® 75 prep grade) equilibrated in TBS (150 mM NaCl, 25 mM Tris-Cl, pH 7.5). The peak of the folded class I protein is identified by analysis of the samples with SDS polyacrylamide gel electrophoresis: it contains heavy and light chains and has an apparent molecular weight of approximately 60000 Da.

The corresponding fractions are unified. The protein concentration is determined as described above.

Production of a Class I Tetramer

Folded MHC class I proteins are received at a concentration of 5 μM in a biotinylation buffer (50 mM Tris-Cl pH 7.4; 150 mM NaCl; 1 mM biotin; 5 mM adenosine triphosphate; 5 mM MgCl₂) and mixed with 0.1 μM of a recombinant BirA-biotinylation enzyme. The reaction is incubated at 25° C. for 12 hours.

The tetramerization is induced by adding 20 μM of fluorescently labeled avidine or streptavidine (e.g., phycoerythrine-conjugated ultravidine, Leinco) and the reaction is incubated for 15 minutes at 4° C.

The tetramer complexes are cleaned by gel filtration in a SUPERDEX® S-200 column (equilibrated in TBS (25 mM Tris-Cl pH 7.4; 150 mM NaCl)).

The corresponding fractions are unified. The protein concentration is determined as described above.

Addition of the Examination Peptide

In order to obtain a peptide-bonded tetramer, a solution of the tetramer is mixed in TBS with 10 μM of the corresponding examination peptide and with 10 mM of the ligand exchanger/ligand releaser (or at the respectively suitable concentration, depending on the chemical nature of the ligand exchanger/ligand releaser). The reaction is incubated at 25° C. for 15 minutes.

If necessary, the peptide tetramer complexes are cleaned with a SUPERDEX® S-200 column (equilibrated in TBS). The corresponding fractions are unified. The protein concentration is determined as described above.

Reaction of the Tetramer with T-Cells and Flow Cytometry 200,000 isolated T-cells (the number is determined under a microscope by means of a Neugebauer chamber) are mixed in a 1 mL FACS buffer (TBS plus 2% fetal calf serum and 4 mM NaN₃) with a cleaned peptide tetramer complex to a final concentration of 0.5 mg/ml. The reaction is incubated at 4° C. for one hour.

The cells are centrifuged (800×g, 5 minutes, 4° C.) and the supernatant is disposed of. The cells are washed twice with an FACS buffer and then resuspended in a fixation buffer (PBS, 2% paraformaldehyde).

The flow cytometry is implemented via a commercially available device (for example, BD FACSARIA® or Partec CYFLOW® Space).

Example 2

The following describes the use of the kit. A kit containing a pre-solution examination reagent is provided.

In order to obtain an examination reagent, the pre-solution of the pre-solution examination reagent is mixed with 10 μM of the corresponding examination peptide and 10 μM of the ligand exchanger/ligand releaser (or at the respectively suitable concentration, depending the chemical nature of the ligand exchanger/ligand releaser). The reaction is incubated at 25° C. for 15 min.

If necessary, the examination reagent is cleaned by gel filtration with a SUPERDEX® S-200 column (equilibrated in TBS). The corresponding fractions are unified. The protein concentration is determined as described above.

The reaction of the examination reagent with T-cells and the detection of the complexes take place as described above.

Example 3

In the following the method according to the present invention is described in more detail based on a concrete exemplary embodiment.

First the murine MHC class I protein H-2K$^b$ is produced in *E. coli* cells in accordance with the method described above and provided with a biotin molecule. It is then folded, according to the method described above, together with human beta-2-microglobulin also produced in *E. coli* cells and with the helper ligand phenylalanyl-alanyl-propyl-glycyl-asparaginyl-tyrosyl-propyl-alanyl-leucine (SEQ ID NO: 2), i.e., a peptide of the sequence FAPGNYPAL (the letters of the peptide sequence correspond to the one letter code for amino acids according to the provisions of the International Union for Pure and Applied Chemistry). The helper ligand FAPGNYPAL is then exchanged according to the method described above by means of the ligand exchanger/ligand releaser glycyl-leucine, i.e., a peptide of the sequence GL with the examination peptide seryl-isoleucyl-isoleucyl-asparaginyl-phenylalanyl-glytamyl-lysyl-leucine (SEQ ID NO: 3), i.e., a peptide of the sequence SIINFEKL. The complex is then mixed according to the method described above with streptavidin, which has been chemically bonded with the fluorescent dye fluorescein and subsequently cleaned. An examination reagent is produced in this manner, which is subsequently diluted and mixed with the T-cell clone B3Z, which carries a T-cell receptor that binds with the complex formed by H-2K$^b$ and SIINFEKL SEQ ID NO: 3. The cells colored in this manner are then analyzed in a flow cytometer.

The present invention is not limited to embodiments described herein; reference should be had to the appended claims.

LIST OF REFERENCE NUMERALS 1 unfolded MHC class I protein
2 examination peptide
3 procedure for folding the MHC class I protein with the examination peptide
4 MHC class I protein folded with a bonded examination peptide
5 precursor of the anchor element, here: reagent for biotinylation
6 biotinylation procedure
7 MHC class I protein folded with a bonded examination peptide and biotinylated
8 multimerization element, here: streptavidin
9 procedure for binding (7) with (8)
10 multimer, here: tetramer with the examination peptide (2)
11 examination peptide (chemically different from (2))
12 multimer, here: tetramer with the examination peptide (11)
13 helper ligand
14 procedure for folding the MHC class I protein with the helper ligand
15 MHC class I protein folded with the bonded helper ligand
16 procedure for biotinylation
17 MHC class I protein folded with the bonded helper ligand and anchor element (e.g., biotin)
18 procedure for binding (17) with streptavidin
19 multimer with MHC class I proteins with a bonded helper ligand
20 examination peptide
21 ligand exchanger/ligand releaser
22 procedure for exchanging the helper ligand with the examination peptide (20) by means of the ligand exchanger/ligand releaser
23 multimer, here: tetramer with the examination peptide (20)
24 examination peptide (chemically different from (20))
25 procedure for exchanging the helper ligand with the examination peptide (24) by means of the ligand exchanger/ligand releaser
26 multimer, here: tetramer with the examination peptide (24)

What is claimed is:

1. A method for producing an examination reagent, the method comprising:
   providing and adding a helper ligand peptide to an unfolded MHC class I receptor protein and β2m in order to produce a folded MHC class I receptor protein, wherein the helper ligand peptide consists of a peptide of 8 to 11 amino acid residues in length and has a lower affinity for a folded MHC class I receptor protein than that of an examination peptide of interest;
   adding a glycyl-leucine (GL) dipeptide as a ligand exchanger/ligand releaser to the folded MHC class I receptor protein, wherein the GL dipeptide has a lower affinity for the folded MHC class I receptor protein than the affinity of the helper ligand peptide for the folded MHC class I receptor protein; and
   adding an examination peptide having a higher affinity for the folded MHC class I receptor protein than the affinity of the helper ligand peptide for the folded MHC class I receptor protein, so that the examination peptide is exchanged for the helper ligand peptide, thereby providing the examination reagent, and wherein the MHC class I receptor protein is H-2K$^b$.

2. The method as recited in claim 1, wherein the β2m is human β2m.

3. The method as recited in claim 1, wherein the helper ligand peptide is FAPGNYPAL (SEQ ID NO: 2) and the β2m is human β2m.

4. The method as recited in claim 1, wherein the unfolded MHC class I receptor protein is produced in an expression system.

5. The method as recited in claim 1, further comprising:
   attaching a signaling element to the unfolded or folded MHC class I receptor protein,
   wherein the signaling element is a fluorescent dye.

6. The method as recited in claim 1, further comprising:
   attaching an anchor element to the unfolded or folded MHC class I receptor protein,
   wherein the anchor element is a biotin molecule.

7. The method as recited in claim 1, further comprising:
   providing a plurality of folded MHC class I receptor proteins and assembling the said plurality of folded MHC class I receptor proteins to form a multimer,
   wherein at least one of the folded MHC class I receptor proteins comprises the helper ligand.

8. The method as recited in claim 7, further comprising:
   attaching a multimer signaling element to the multimer, wherein the multimer signaling element is a fluorescent dye.

* * * * *

SEQUENCE LISTING

```
<160> NUMBER OF SEQ ID NOS: 3

<210> SEQ ID NO 1
<211> LENGTH: 12
<212> TYPE: PRT
<213> ORGANISM: Unknown
<220> FEATURE:
<223> OTHER INFORMATION: Linker

<400> SEQUENCE: 1

Gly Gly Gly Ser Gly Gly Gly Ser Gly Gly Gly Ser
1               5                   10

<210> SEQ ID NO 2
<211> LENGTH: 9
<212> TYPE: PRT
<213> ORGANISM: Unknown
<220> FEATURE:
```

```
<223> OTHER INFORMATION: Helper Ligand

<400> SEQUENCE: 2

Phe Ala Pro Gly Asn Tyr Pro Ala Leu
1               5

<210> SEQ ID NO 3
<211> LENGTH: 8
<212> TYPE: PRT
<213> ORGANISM: Unknown
<220> FEATURE:
<223> OTHER INFORMATION: Examination Peptide

<400> SEQUENCE: 3

Ser Ile Ile Asn Phe Glu Lys Leu
1               5
```